(12) United States Patent  (10) Patent No.: US 7,815,674 B1
Ragazzo                    (45) Date of Patent:     Oct. 19, 2010

(54) SELF-EXPANDING STENT SYSTEM

(76) Inventor: John R. Ragazzo, 11119 Eagle Bend Dr., Hudson, FL (US) 34667

( * ) Notice: Subject to any disclaimer, the term of this patent is extended or adjusted under 35 U.S.C. 154(b) by 543 days.

(21) Appl. No.: 11/191,109

(22) Filed: Jul. 27, 2005

(51) Int. Cl.
A61F 2/06 (2006.01)
(52) U.S. Cl. .................................................. 623/1.23
(58) Field of Classification Search ............. 623/1.23, 623/1.2, 1.15, 23.7
See application file for complete search history.

(56) References Cited

U.S. PATENT DOCUMENTS

| | | | | |
|---|---|---|---|---|
| 4,665,918 A | * | 5/1987 | Garza et al. | 606/108 |
| 5,282,824 A | * | 2/1994 | Gianturco | 623/1.13 |
| 5,342,387 A | * | 8/1994 | Summers | 606/198 |
| 5,354,309 A | * | 10/1994 | Schnepp-Pesch et al. | 606/198 |
| 5,378,239 A | * | 1/1995 | Termin et al. | 604/104 |
| 5,645,559 A | * | 7/1997 | Hachtman et al. | 623/1.2 |
| 5,954,744 A | * | 9/1999 | Phan et al. | 606/198 |
| 5,954,765 A | * | 9/1999 | Ruiz | 623/1.15 |
| 6,099,536 A | * | 8/2000 | Petillo | 606/142 |
| 6,241,738 B1 | * | 6/2001 | Dereume | 606/108 |
| 6,254,592 B1 | | 7/2001 | Samson et al. | |
| 6,273,908 B1 | * | 8/2001 | Ndondo-Lay | 623/1.43 |
| 6,280,465 B1 | | 8/2001 | Cryer | |
| 6,319,277 B1 | | 11/2001 | Rudnick et al. | |
| 6,395,017 B1 | * | 5/2002 | Dwyer et al. | 623/1.11 |
| 6,425,915 B1 | | 7/2002 | Khosravi et al. | |
| 2003/0074082 A1 | * | 4/2003 | Bottcher et al. | 623/23.7 |
| 2003/0109930 A1 | * | 6/2003 | Bluni et al. | 623/23.7 |

* cited by examiner

Primary Examiner—Gary Jackson
Assistant Examiner—Son Dang
(74) Attorney, Agent, or Firm—Edward P Dutkiewicz

(57) ABSTRACT

An elongated generally cylindrical stent, fabricated of a resilient material, has a pair of side ends with a top end and a bottom end. The bottom end has a central spine along the entire extent of the stent. The central spine has a plurality of interleafing ribs. Each rib has a lower end coupled to the central spine and an upper free end. A holding sleeve shaped in an elongated, generally cylindrical configuration is fabricated of a resilient material. The sleeve is hollow with an inside cylindrical surface and an outside cylindrical surface and has an open application end.

7 Claims, 3 Drawing Sheets

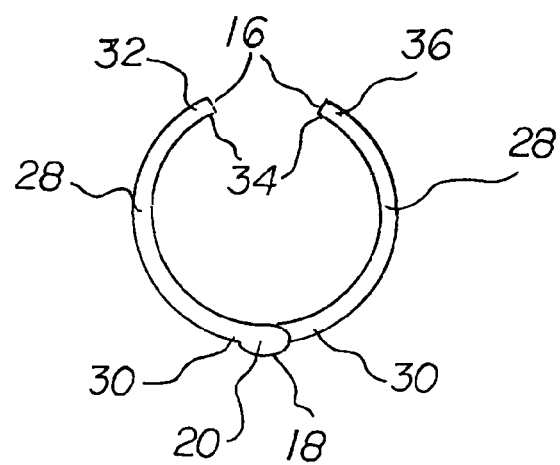
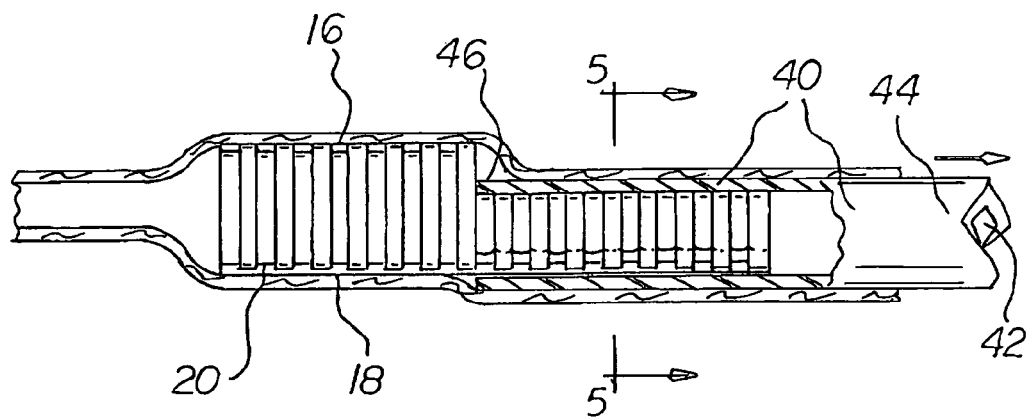

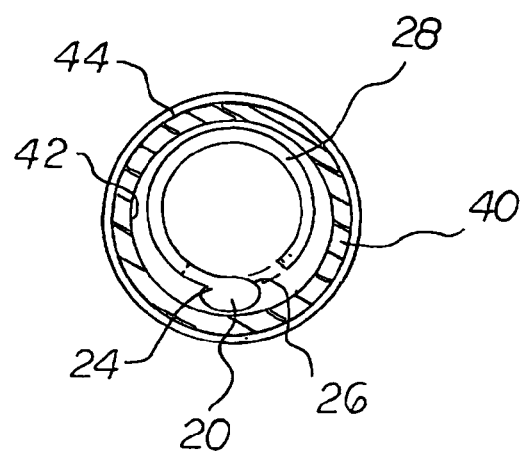
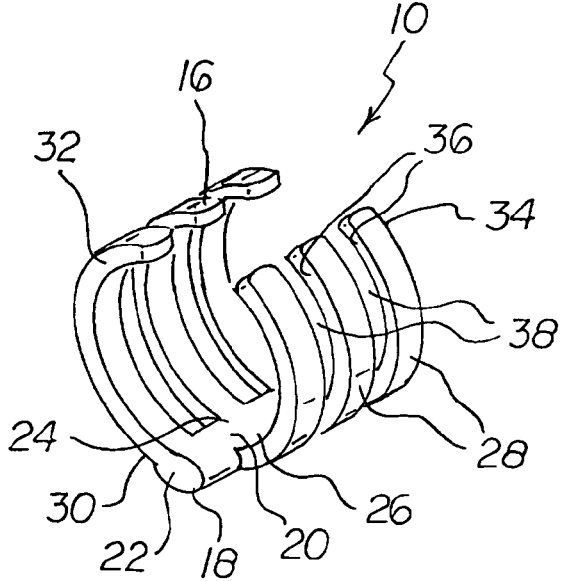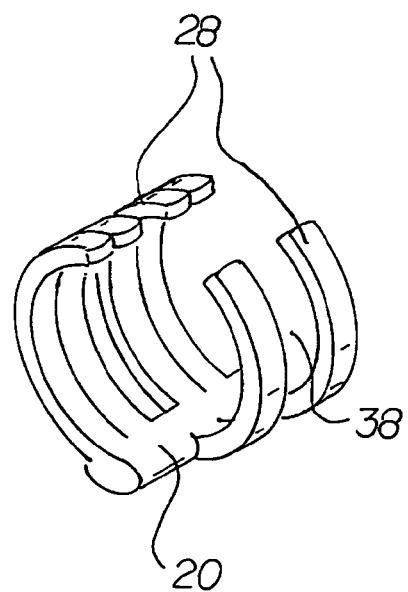

SELF-EXPANDING STENT SYSTEM

BACKGROUND OF THE INVENTION

1. Field of the Invention

The present invention relates to a self-expanding stent system and more particularly pertains to providing force to open a partially closed vasculature without the use of a balloon applicator.

2. Description of the Prior Art

The use of stent systems of known designs and configurations is known in the prior art. More specifically, stent systems of known designs and configurations previously devised and utilized for the purpose of opening partially closed vasculatures are known to consist basically of familiar, expected, and obvious structural configurations, notwithstanding the myriad of designs encompassed by the crowded prior art which has been developed for the fulfillment of countless objectives and requirements.

By way of example, U.S. Pat. No. 6,254,592 issued Jul. 3, 2001 to Samson et al. discloses a Variable Stiffness Coils. U.S. Pat. No. 6,280,592 issued Aug. 28, 2001 to Cryer discloses an Apparatus and Method for Delivering a Self Expanding Stent on a Guide Wire. U.S. Pat. No. 6,319,277 issued Nov. 20, 2001 to Rudnick et al. discloses a Nested Stent. Lastly, U.S. Pat. No. 6,425,915 issued Jul. 30, 2002 to Khosravi et al. discloses a Helical Mesh Endoprosthesis and Methods of Use.

While these devices fulfill their respective, particular objectives and requirements, the aforementioned patents do not describe a self-expanding stent system that allows providing force to open a partially closed vasculature without the use of a balloon applicator.

In this respect, the self-expanding stent system according to the present invention substantially departs from the conventional concepts and designs of the prior art and in doing so provides an apparatus primarily developed for the purpose of providing force to open a partially closed vasculature without the use of a balloon applicator.

Therefore, it can be appreciated that there exists a continuing need for a new and improved self-expanding stent system which can be used for providing force to open a partially closed vasculature without the use of a balloon applicator. In this regard, the present invention substantially fulfills this need.

SUMMARY OF THE INVENTION

In view of the foregoing disadvantages inherent in the known types of stent systems of known designs and configurations now present in the prior art, the present invention provides an improved self-expanding stent system. As such, the general purpose of the present invention, which will be described subsequently in greater detail, is to provide a new and improved self-expanding stent system and method which has all the advantages of the prior art and none of the disadvantages.

To attain this, the present invention essentially comprises first a stent. The stent is in a generally cylindrical configuration and is fabricated of a resilient material that can be adapted to hold a charged polarity and capable of retaining memory. The resilient material is selected from the class of memory retaining materials including, but not limited to, plastic and metal. The stent has a pair of side ends, a top end and a bottom end. The bottom end has a central spine along the entire extent of the stent between the side ends. The central spine has a pair of end portions, a first edge and a second edge. The central spine also has a plurality of interleafing ribs. The ribs extend from the central spine in an alternating fashion along opposite edges of the spine. Each rib is resilient and has a semicircular configuration. Each rib has a lower end coupled to the central spine, an upper free end with a beveled surface and a pair of side faces. The side faces of adjacent ribs contact each other at the top ends of the stents. Rib spaces between each rib are adapted to receive the corresponding ribs on the opposite edges of the central spine.

The stent has a first resting orientation. In the resting orientation the ribs are extended so that compressing the ribs around the spine will develop force that wants to return to the resting position. The ribs are in a cylindrical configuration with a first diameter in the resting orientation. The stent also has a second compressed orientation. In the compressed orientation, the ribs are compressed under a force and there is a relatively large amount of over lap between the side faces of adjacent ribs. The stent is in a cylindrical configuration with a second diameter wherein the second diameter is less than the first diameter in the compressed orientation.

Lastly, a holding sleeve is provided. The holding sleeve is fabricated of a resilient material. The holding sleeve is in an elongated, hollow cylindrical configuration with an inside cylindrical surface, an outside cylindrical surface and an open application end. The holding sleeve is adapted to be inserted in a vasculature. The holding sleeve has a third diameter approximate to the second diameter. The holding sleeve is adapted to carry the stent in the compressed orientation in the vasculature to a position where the user desires to open the stent. The user then removes the stent out through the open application end of the holding sleeve. The stent will then apply force to return to the resting orientation under the resilient power of the material thereby opening the vasculature.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims attached.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved self-expanding stent system which has all of the advantages of the prior art stent systems of known designs and configurations and none of the disadvantages.

It is another object of the present invention to provide a new and improved self-expanding stent system which may be easily and efficiently manufactured and marketed.

It is further object of the present invention to provide a new and improved self-expanding stent system which is of durable and reliable constructions.

An even further object of the present invention is to provide a new and improved self-expanding stent system which is susceptible of a low cost of manufacture with regard to both materials and labor, and which accordingly is then susceptible of low prices of sale, thereby making such self-expanding stent system economically available.

Another capability of this invention is to provide for polarity in materials or coatings that can resist subsequent reclosure of the vasculature.

Even still another object of the present invention is to provide a self-expanding stent system for providing force to open a partially closed vasculature without the use of a balloon applicator.

Further, the stent will be capable of using coatings to enhance performance for insertion and resistance to further closure of the vasculature.

Lastly, it is an object of the present invention to provide a new and improved self-expanding stent system having a stent shaped in an elongated, generally cylindrical configuration and fabricated of a resilient material. The stent has a pair of side ends with a top end and a bottom end. The bottom end has a central spine along the entire extent of the stent. The central spine has a plurality of inter-leafing ribs. Each rib has a lower end coupled to the central spine and an upper free end. A holding sleeve shaped in an elongated, generally cylindrical configuration is fabricated of a resilient material. The sleeve is hollow with an inside cylindrical surface and an outside cylindrical surface and has an open application end.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there are illustrated preferred and alternate embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 3 is an end elevational view of the present invention taken along line 3-3 of FIG. 1.

FIG. 4 is a cross sectional view of the present invention showing holding sleeve inserting a stent into vasculature.

FIG. 5 is a cross sectional view of the present invention in use taken along line 5-5 of FIG. 4.

FIG. 6 is a perspective illustration of the present invention showing the interlocking of every other rib.

FIG. 7 is a perspective illustration of an alternative embodiment of the present invention.

The same reference numerals refer to the same parts throughout the various Figures illustrating the primary and alternate embodiments of the present invention.

DESCRIPTION OF THE PREFERRED EMBODIMENT

Figure 1:
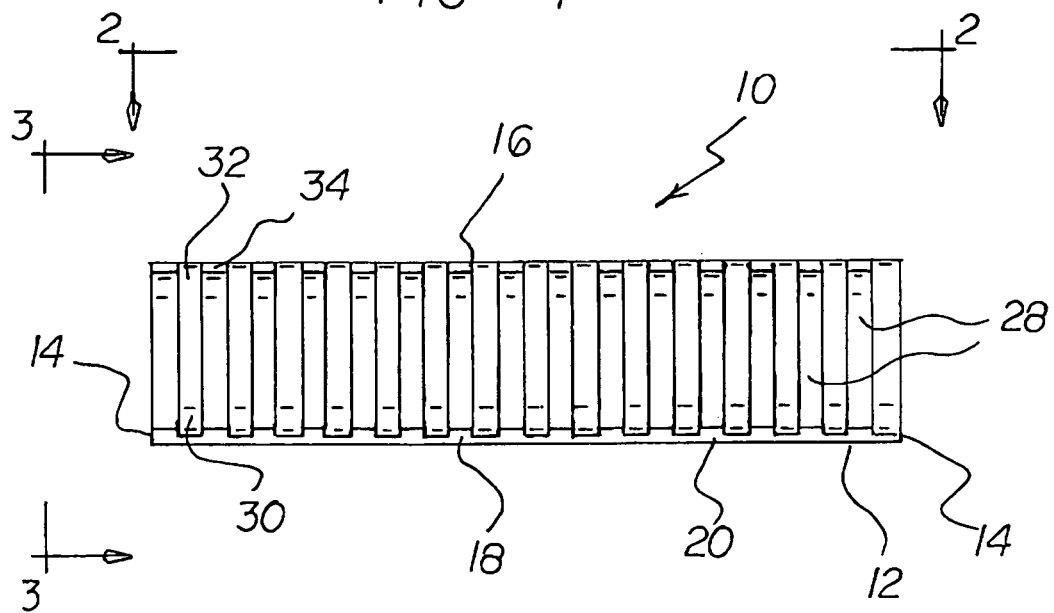
FIG. 1 is a front elevational illustration of the preferred embodiment of the present invention.

With reference now to the drawings, and in particular to FIG. 1 thereof, the preferred embodiment of the new and improved self-expanding stent system embodying the principles and concepts of the present invention and generally designated by the reference numeral 10 will be described.

The present invention, the self expanding stent system 10 for providing force to open a partially closed vasculature without the use of a balloon applicator is comprised of a plurality of components. Such components in their broadest context include a stent and a holding sleeve. Such components are individually configured and correlated with respect to each other so as to attain the desired objective.

Figure 2:
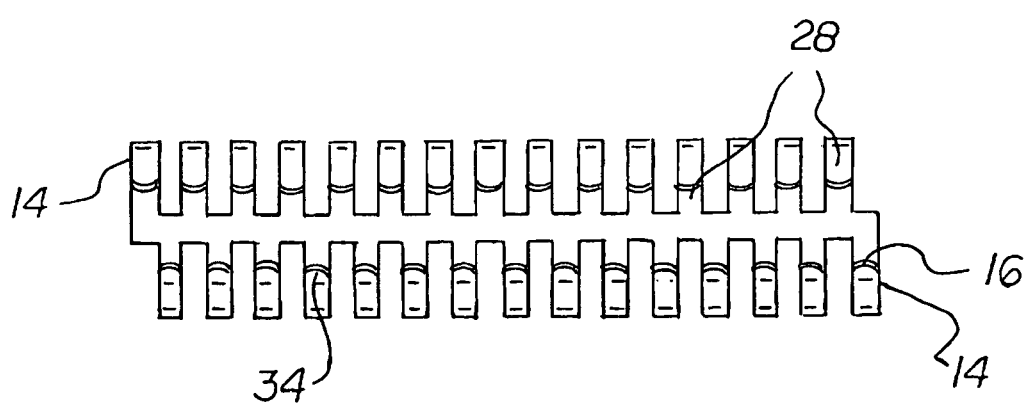
FIG. 2 is plan view of the present invention taken along line 2-2 of the FIG. 1.

First provided is a stent 12. The stent is in a generally cylindrical configuration and is fabricated of a resilient material that is adapted to hold a charged polarity which is adapted to be used with performance enhancing coatings and which is capable of retaining memory. The cylindrical configuration of the stent has a circular cross section or an oblong cross section. The resilient material is selected from the class of memory retaining materials including, but not limited to, plastic and metal. The stent has a pair of side end ribs 14, a top end 16 and a bottom end 18. The bottom end has a central spine 20 along the entire extent of the stent between the side ends. The central spine has a pair of end portions 22, a first edge 24 and a second edge 26. The central spine also has a plurality of inter-leafing ribs 28. The interleafing ribs consist of a pair of side end ribs with there being located between the side ribs a plurality of intermediate ribs. The intermediate ribs each having two oppositely located ribs. Each rib has a lower end coupled to the central spine and an upper free end. Each rib interdigitates with, and is nested between, two adjacently located opposite ribs. Each rib has a width and a length as can be seen in FIG. 3. Each rib width is constant along the length of each rib, as shown in FIGS. 1 and 2. In this way, each intermediate rib contacts adjacent ribs along its length, as shown in FIG. 1. This provides a smooth outer surface when the stent is in a compressed configuration, as shown in FIG. 1. The ribs extend from the central spine in an alternating fashion along opposite edges of the spine. Each rib is resilient and has a semicircular configuration. Each rib has a lower end 30 coupled to the central spine, an upper free end 32 with a beveled surface 34 and a pair of side faces 36. The side faces of adjacent ribs contact each other at the top ends of the stents. Each rib is nested within the two ribs which are located opposite of, and to either side of, the rib, and the spine, except for the first and last rib which only have one rib on one side. This configuration gives the exterior of the stent a smooth surface. Rib spaces 38 between each rib are adapted to receive the corresponding ribs on the opposite edges of the central spine.

The stent has a first resting orientation. In the resting orientation the ribs are extended so that compressing the ribs around the spine will develop a force that wants to return to the resting position. The ribs are in a cylindrical configuration with a first diameter in the resting orientation. The stent also has a second compressed orientation. In the compressed orientation, the ribs are compressed under a force and there is a relatively large amount of over lap between the side faces of adjacent ribs. The stent is in a cylindrical configuration with a second diameter wherein the second diameter is less than the first diameter in the compressed orientation.

Lastly, a holding sleeve 40 is provided. The holding sleeve is fabricated of a resilient material. The holding sleeve is in an elongated, hollow cylindrical configuration with an inside cylindrical surface 42, an outside cylindrical surface 44 and an open application end 46. The holding sleeve is adapted to be inserted in a vasculature. The holding sleeve has a third diameter approximate to the second diameter. The holding sleeve is adapted to carry the stent in the compressed orientation in the vasculature to a position where the user desires to open the stent. The user then removes the stent out through the open application end of the holding sleeve. The stent will then return to the resting orientation under the resilient power of the material thereby opening the vasculature to the first diameter of the stent.

In the preferred embodiment of the invention, as shown in FIGS. 1 through 6, the ribs interlock in a one-to-one fashion. In an alternate embodiment of the invention, as shown in FIG. 7, the ribs interlock in a two-to-one fashion.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A self expanding stent system comprising:
    a stent shaped in an elongated, generally cylindrical configuration and fabricated of a resilient material, the stent having a pair of side ends with a top end and a bottom end, the bottom end having a central spine along the entire extent of the stent, the central spine having a plurality of inter-leafing ribs, the interleafing ribs consisting of a pair of side end ribs with there being located between the side ribs a plurality of intermediate ribs each having two oppositely located ribs, each rib having a lower end coupled to the central spine and an upper free end, with each rib interdigitating with and being nested between two adjacently located opposite ribs and each rib having a width and a length, the width of each rib being constant along the length of each rib; and
    a holding sleeve shaped in an elongated, generally cylindrical configuration and fabricated of a resilient material, the sleeve being hollow with an inside cylindrical surface and an outside cylindrical surface and with an open application end; wherein the ribs include a pair of side faces such that the side faces of adjacent ribs contact each other at the top end of the stent.

2. The self expanding stent system as set forth in claim 1 wherein the ribs extend from the central spine in an alternating fashion along opposite edges of the spine.

3. The self expanding stent system as set forth in claim 1 wherein the ribs interlock in a one-to-one fashion.

4. The self expanding stent system as set forth in claim 1 wherein the stent has a generally cylindrical configuration with a circular cross section.

5. The self expanding stent system as set forth in claim 1 wherein the stent has a generally cylindrical configuration with an oblong cross section.

6. The self expanding stent system as set forth in claim 1 wherein the ribs interlock in a two-to-one fashion.

7. A self expanding stent system for providing force to open a partially closed vasculature without the use of a balloon applicator comprising, in combination:
    a stent having a generally cylindrical configuration and being fabricated of a resilient material that is adapted to hold a charged polarity and is capable of retaining memory and is adapted to be used with performance enhancing coatings, the resilient material selected from the class of memory retaining materials including plastic and metal, the stent having a pair of side ends, a top end, and a bottom end, the bottom end having a central spine along the entire extent of the stent between the side ends with the central spine having a pair of end portions, a first edge and a second edge, the central spine having a plurality of inter-leafing ribs extending from the central spine in an alternating fashion along opposite edges of the spine, each rib being resilient and having a semicircular configuration with a lower end coupled to the central spine, an upper free end with a beveled surface and a pair of side faces such that the side faces of adjacent ribs contact each other at the top ends of the stent, each rib having a width and a length, the width of each rib being constant along the length of each rib, the stent having rib spaces between each rib and adapted to receive the corresponding ribs on the opposite edges of the central spine so that the ribs interdigitate and are nested between the two opposite adjacent ribs and the spine of the stent, each stent having a first resting orientation and having a cylindrical configuration with a first diameter, the stent also having a second compressed orientation wherein the ribs are compressed under a force and having a relatively large amount of over lap between the side faces of adjacent ribs and having a cylindrical configuration with a second diameter wherein the second diameter is less than the first diameter; and
    a holding sleeve fabricated of a resilient material in an elongated, hollow cylindrical configuration with an inside cylindrical surface, an outside cylindrical surface and an open application end, the holding sleeve being adapted to be inserted in a vasculature, the holding sleeve having a third diameter being approximate to the second diameter, the holding sleeve being adapted to carry the stent in the compressed orientation in the vasculature to a position where the user desires to open the stent, where after the user removes the stent out through the open application end of the holding sleeve whereupon the stent will return to the resting orientation under the resilient power of the material thereby opening the vasculature to the first diameter of the stent wherein the ribs include a pair of side faces such that the side faces of adjacent ribs contact each other at the top end of the stent.

* * * * *